United States Patent
Stevens et al.

(10) Patent No.: US 10,274,416 B2
(45) Date of Patent: Apr. 30, 2019

(54) PEEL ADHESION TEST SPECIMENS AND METHOD FOR THEIR PREPARATION

(71) Applicant: The Boeing Company, Chicago, IL (US)

(72) Inventors: Barton E. Stevens, Summerville, SC (US); Katherine L. Frank, Charleson, SC (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/599,209

(22) Filed: May 18, 2017

(65) Prior Publication Data

US 2018/0335379 A1    Nov. 22, 2018

(51) Int. Cl.
*G01N 19/04*    (2006.01)
*G01N 1/44*    (2006.01)
*G01N 3/08*    (2006.01)

(52) U.S. Cl.
CPC ............ *G01N 19/04* (2013.01); *G01N 1/44* (2013.01); *G01N 3/08* (2013.01); *G01N 2203/0091* (2013.01); *G01N 2203/0298* (2013.01)

(58) Field of Classification Search
USPC ............ 156/247, 272.2, 272.6, 273.5, 275.3, 156/275.5, 275.7, 307.1, 307.3, 307.7
See application file for complete search history.

(56) References Cited

U.S. PATENT DOCUMENTS

| 5,246,782 | A | * | 9/1993 | Kennedy | C08J 5/04 428/421 |
| 2010/0028564 | A1 | * | 2/2010 | Cheng | G02B 5/3025 428/1.1 |

OTHER PUBLICATIONS

SAE International. "Aerospace Standard Test Methods for Aerospace Sealants Two-Component Synthetic Rubber Compounds"; AS5127/1, Revision C. Issued May 1997; Revised Oct. 2014.

* cited by examiner

*Primary Examiner* — Sing P Chan
(74) *Attorney, Agent, or Firm* — Perman & Green, LLP

(57) ABSTRACT

A method of preparing specimens for peel-adhesion testing. The method includes applying a first predetermined amount of light-curable material to a substrate coupon, placing a first surface of a substantially transparent peel media in contact with the light-curable material disposed on the substrate coupon, where the substantially transparent peel media includes a second surface spaced from the first surface, and exposing the first predetermined amount of light-curable material disposed between the substrate coupon and the first surface to a light source to cure the first predetermined amount of light-curable material, with light from the light source passing through the substantially transparent peel media to the substrate coupon.

20 Claims, 10 Drawing Sheets

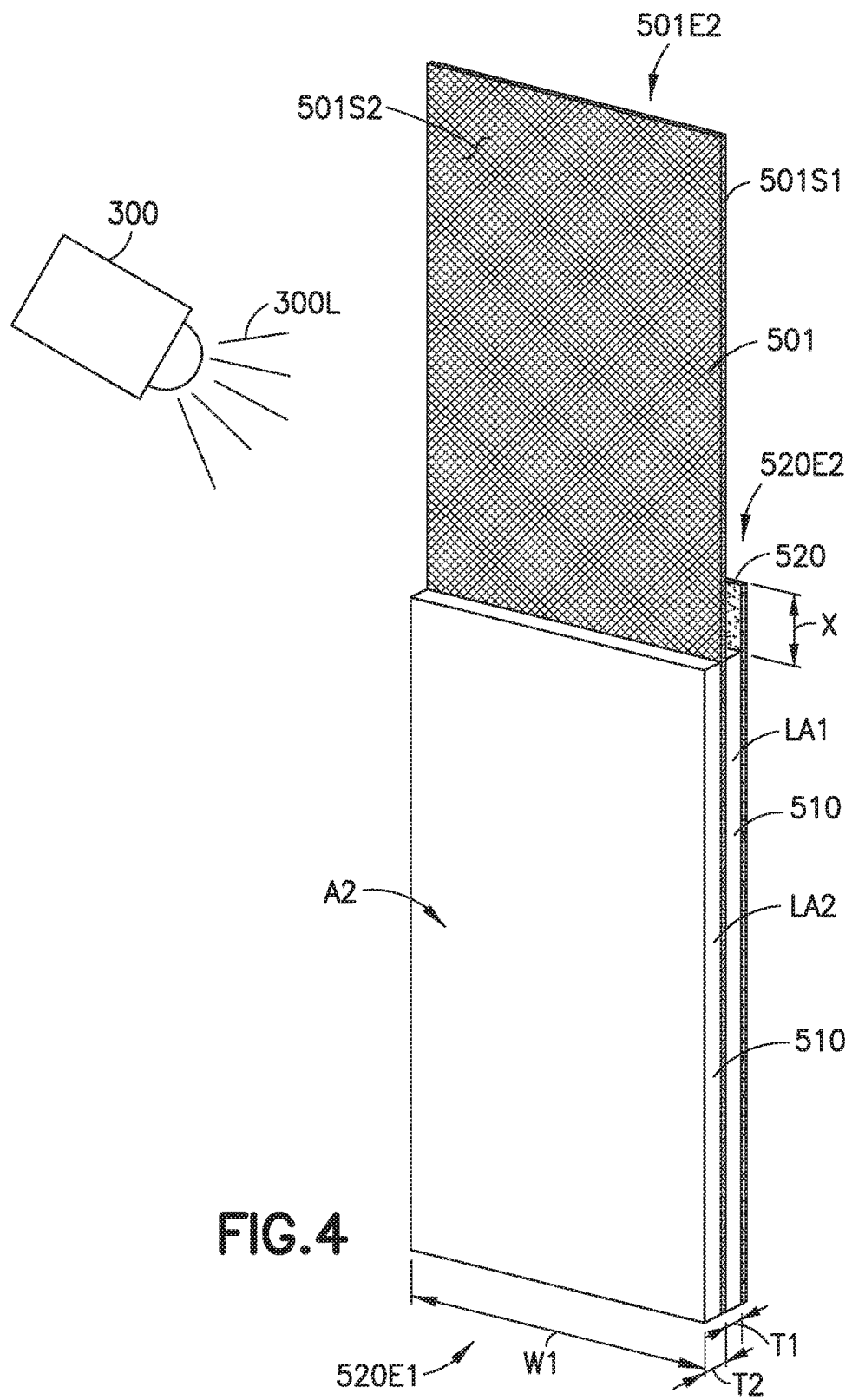

PEEL ADHESION TEST SPECIMENS AND METHOD FOR THEIR PREPARATION

BACKGROUND

1. Field

The aspects of the present disclosure generally relate to peel adhesion testing and in particular, peel adhesion test specimens for light-cured materials.

2. Brief Description of Related Developments

Conventional peel adhesion test specimens have a substrate and an opaque peel media, such as aluminum, adhered to the substrate with a sealant or adhesive to be tested. The opaque peel media peel is gripped by a mechanical testing machine at one end of the adhesion test specimen and the substrate is gripped by the mechanical testing machine on an opposite end of the adhesion test specimen.

The opaque peel media of the conventional peel adhesion test specimens does not allow for light passage and is therefore not suitable for peel adhesion test specimens that are used for testing adhesives and sealants requiring light to cure the adhesives and sealants. For example, conventional peel media include fabric cloth, aluminum and wire mesh. The fabric cloth and aluminum peel media completely block light transmission and are unusable for peel adhesion test specimens for light-cured adhesives and sealants. The wire mesh peel media may allow some light to penetrate through the wire mesh, but the wire mesh produces shadowing within the light-cured adhesives and sealants that affects the cure time of the light-cured adhesives and sealants. For example, if the light-cured sealants are exposed to light for the predetermined amount of time to cure the sealants under normal curing conditions (i.e. where the light is not being blocked in any way by any opaque material) the light cured adhesives and sealants would not be completely cured due to the shadows produced by the wire mesh. On the other hand, to completely cure the light-cured adhesives and sealants covered by the wire mesh, the cure time of the light-cured adhesives and sealants must be increased. This increase in cure time may affect the adhesion properties of the adhesive and sealants compared to curing under normal curing conditions (i.e. the curing of the adhesives and sealants for testing is not the same as the curing of the adhesives and sealants in a production environment). Further, generally conventional peel adhesion test specimens include a substrate, a first layer of adhesive or sealant, the peel media and a second layer of adhesive or sealant on top of the peel media. The use of the wire mesh peel media allows the first and second layers of adhesive or sealant to bond to each other. The adhesives and sealants also are prone to failing at the wire mesh due to, for example, a decreased adhesive area of the wire mesh, where the wire mesh pulls out of the adhesives and sealants during testing. Wire mesh is also abrasive when being handled by humans during peel-adhesion testing.

SUMMARY

The following is a non-exhaustive list of examples, which may or may not be claimed, of the subject matter according to the present disclosure.

One example of the subject matter according to the present disclosure relates to a method of preparing specimens for peel-adhesion testing, the method comprising: applying a first predetermined amount of light-curable material to a substrate coupon; placing a first surface of a substantially transparent peel media in contact with the light-curable material disposed on the substrate coupon, where the substantially transparent peel media includes a second surface spaced from the first surface; and exposing the first predetermined amount of light-curable material disposed between the substrate coupon and the first surface to a light source to cure the first predetermined amount of light-curable material, with light from the light source passing through the substantially transparent peel media to the substrate coupon.

Another example of the subject matter according to the present disclosure relates to a method of preparing specimens for peel-adhesion testing, the method comprising: applying a first predetermined amount of light-curable material to a substrate coupon; activating a first and second surface of a substantially transparent peel media, where the first surface and the second surface are spaced from one another; placing the first surface of the substantially transparent peel media in contact with the light-curable material disposed on the substrate coupon; applying a second predetermined amount of the light-curable material to the second surface of the substantially transparent peel media; and exposing the first predetermined amount of light-curable material and the second predetermined amount of light-curable material to a light source so that the first predetermined amount of light-curable material disposed between the substrate coupon and the first surface and the second predetermined amount of light curable material applied to the second surface of the substantially transparent peel media are cured substantially simultaneously with light from the light source passing through the substantially transparent peel media.

Still another example of the subject matter according to the present disclosure relates to a specimen for peel-adhesion testing, the specimen comprising: a substrate coupon; a first predetermined amount of light-curable material disposed on the substrate coupon; and a substantially transparent peel media having a first surface and a second surface spaced from the first surface, where the substantially transparent peel media is configured so that light passing through the substantially transparent peel media from a light source cures the first predetermined amount of light-curable material to both the substrate coupon and the substantially transparent peel media.

BRIEF DESCRIPTION OF THE DRAWINGS

Figure 1:
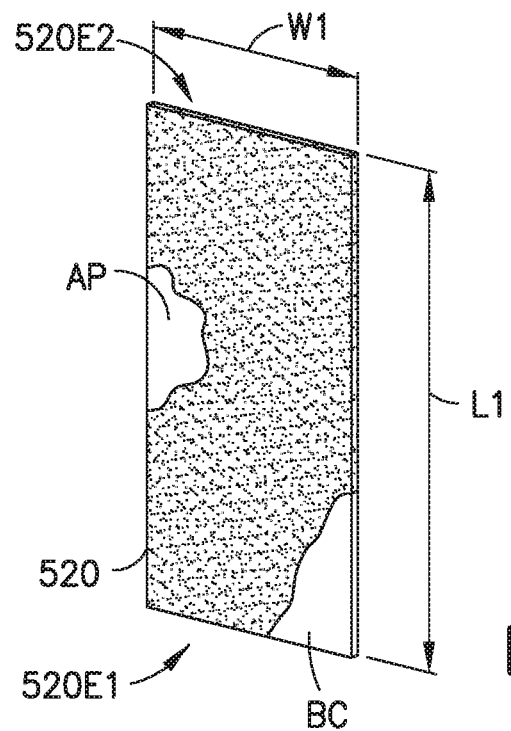
Figure 2:
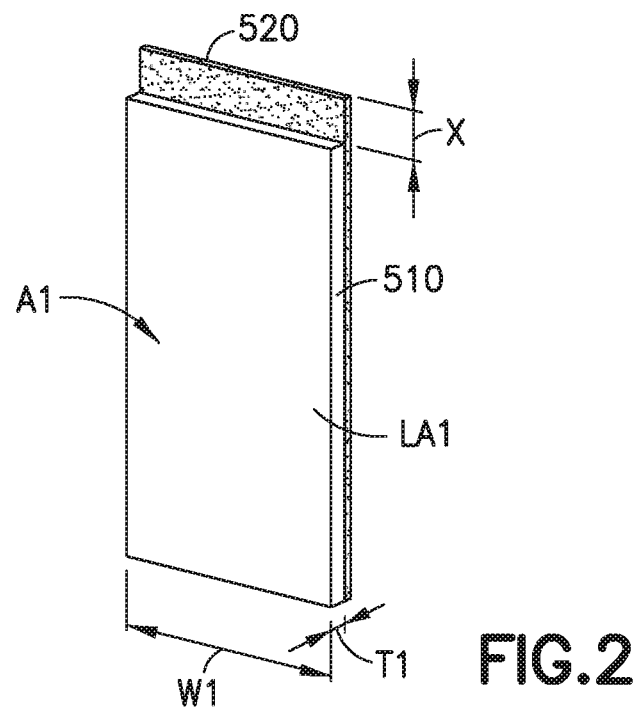
Figure 3:
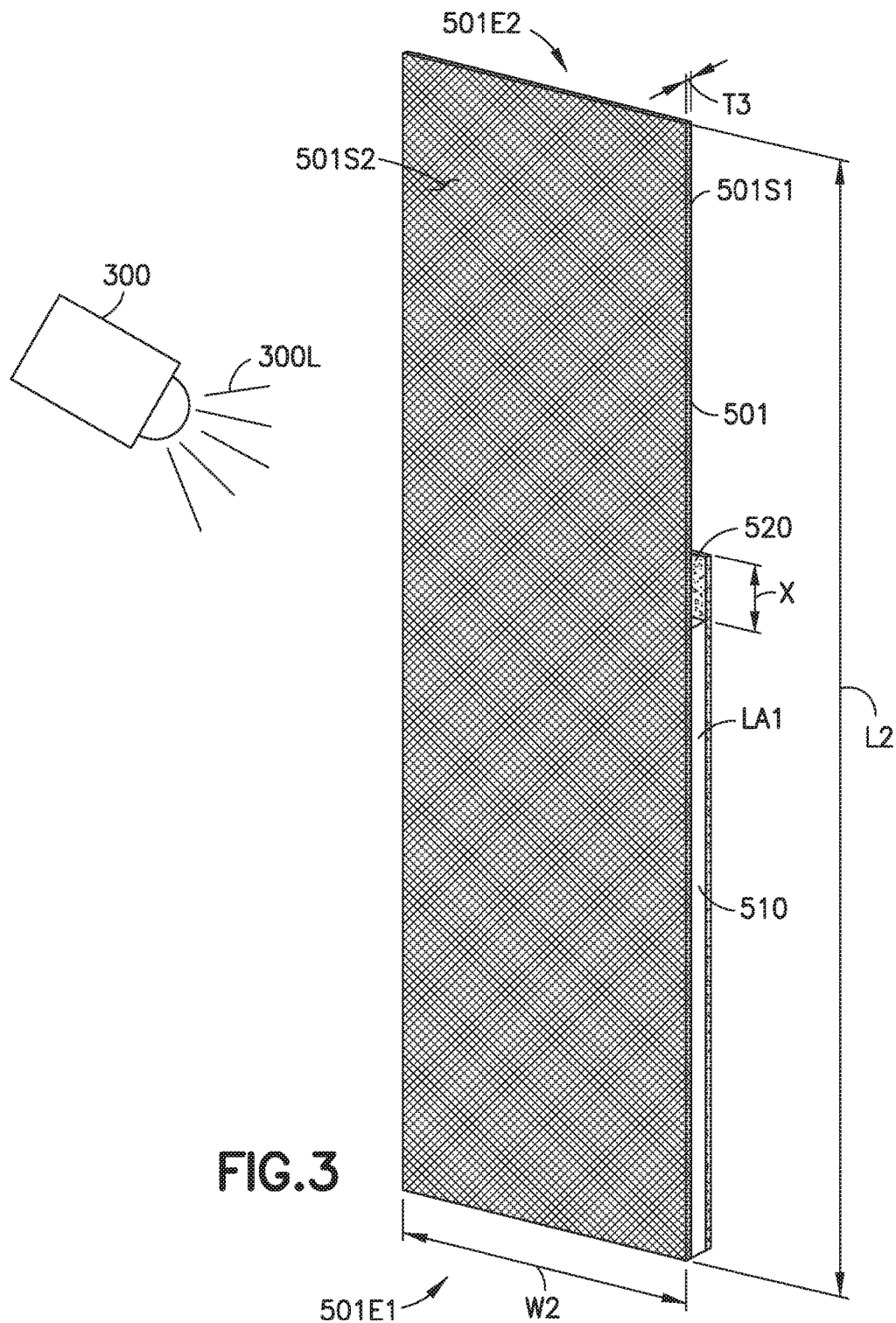
Figure 5A:
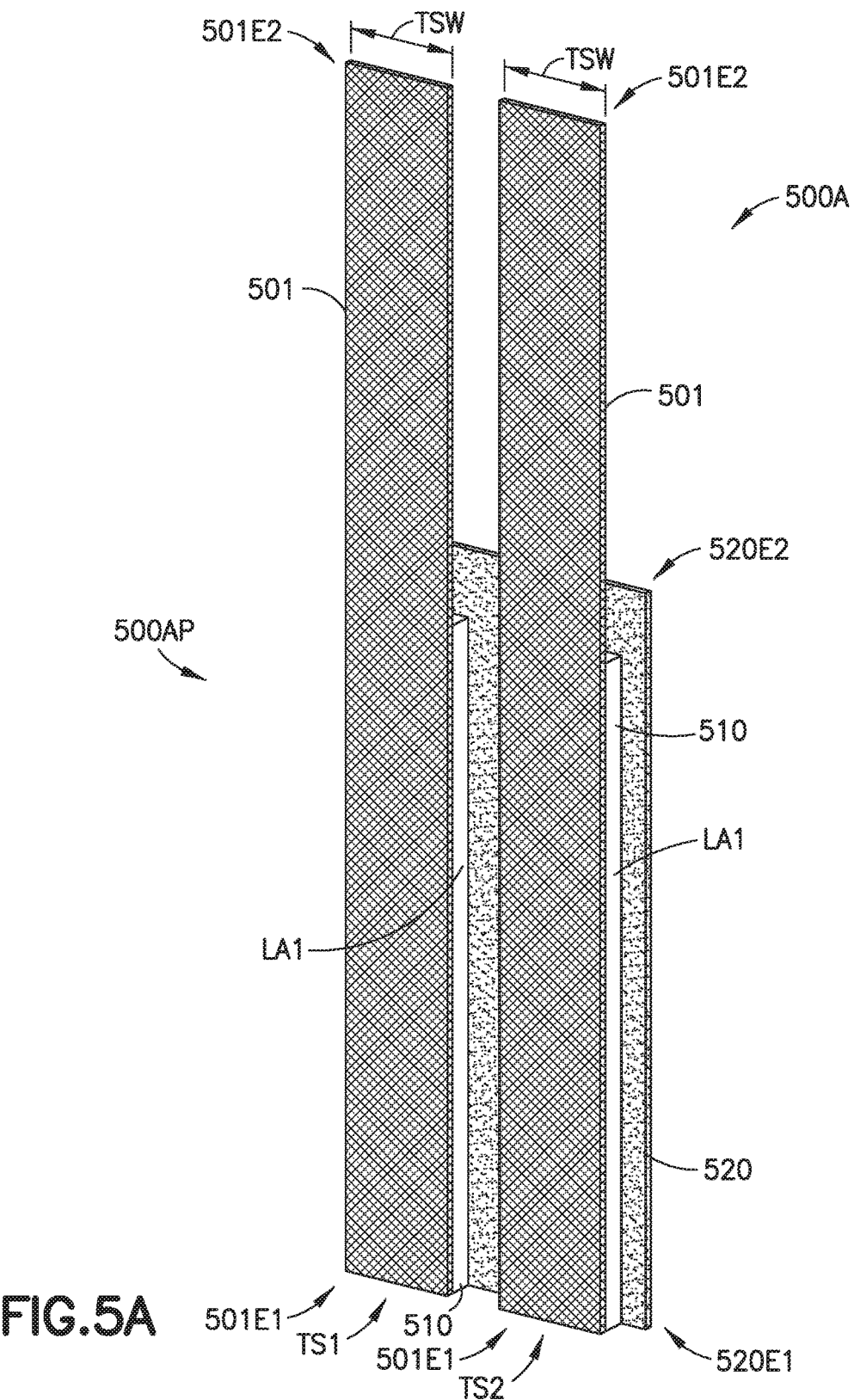
Figure 5B:
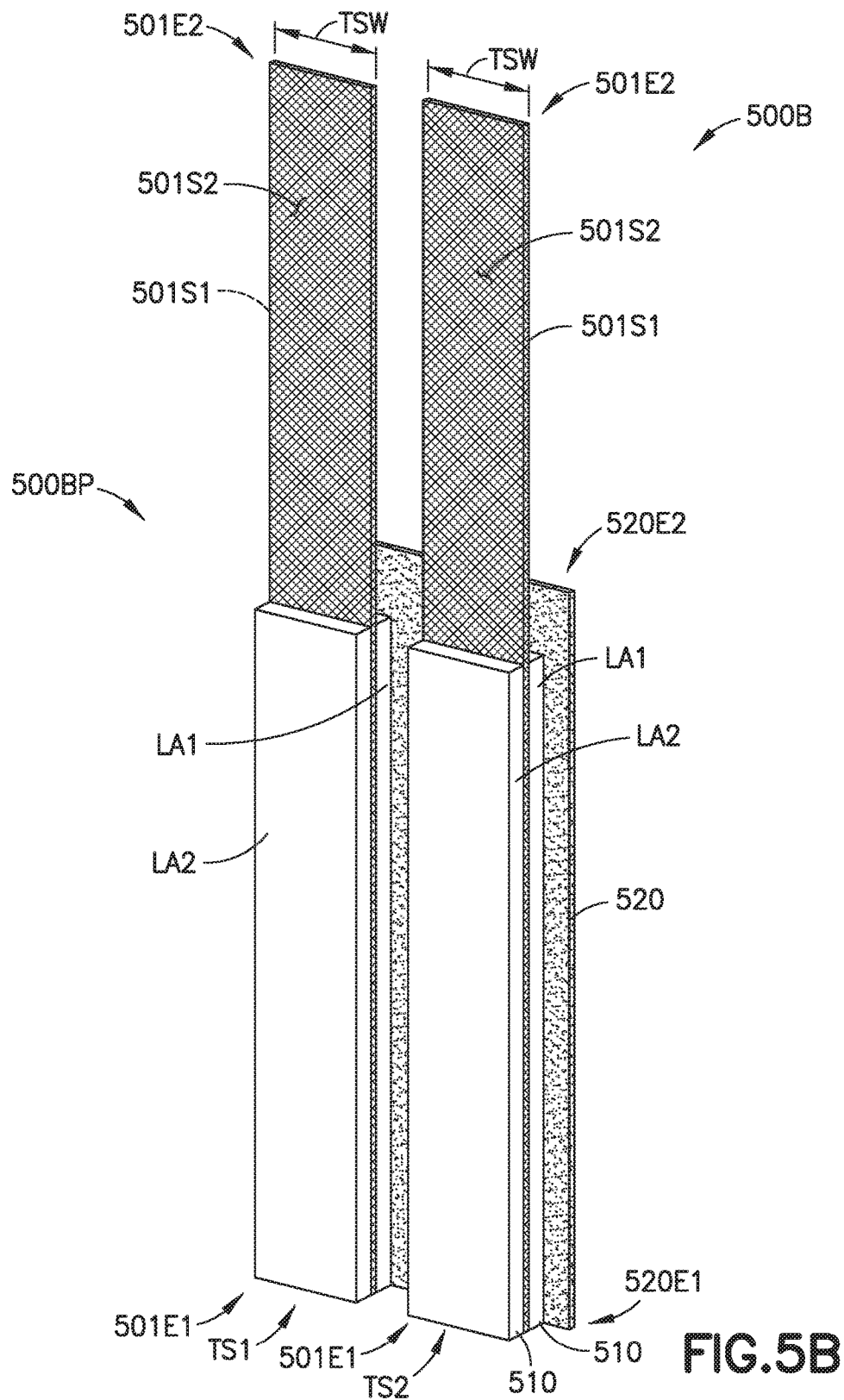
Figure 6:
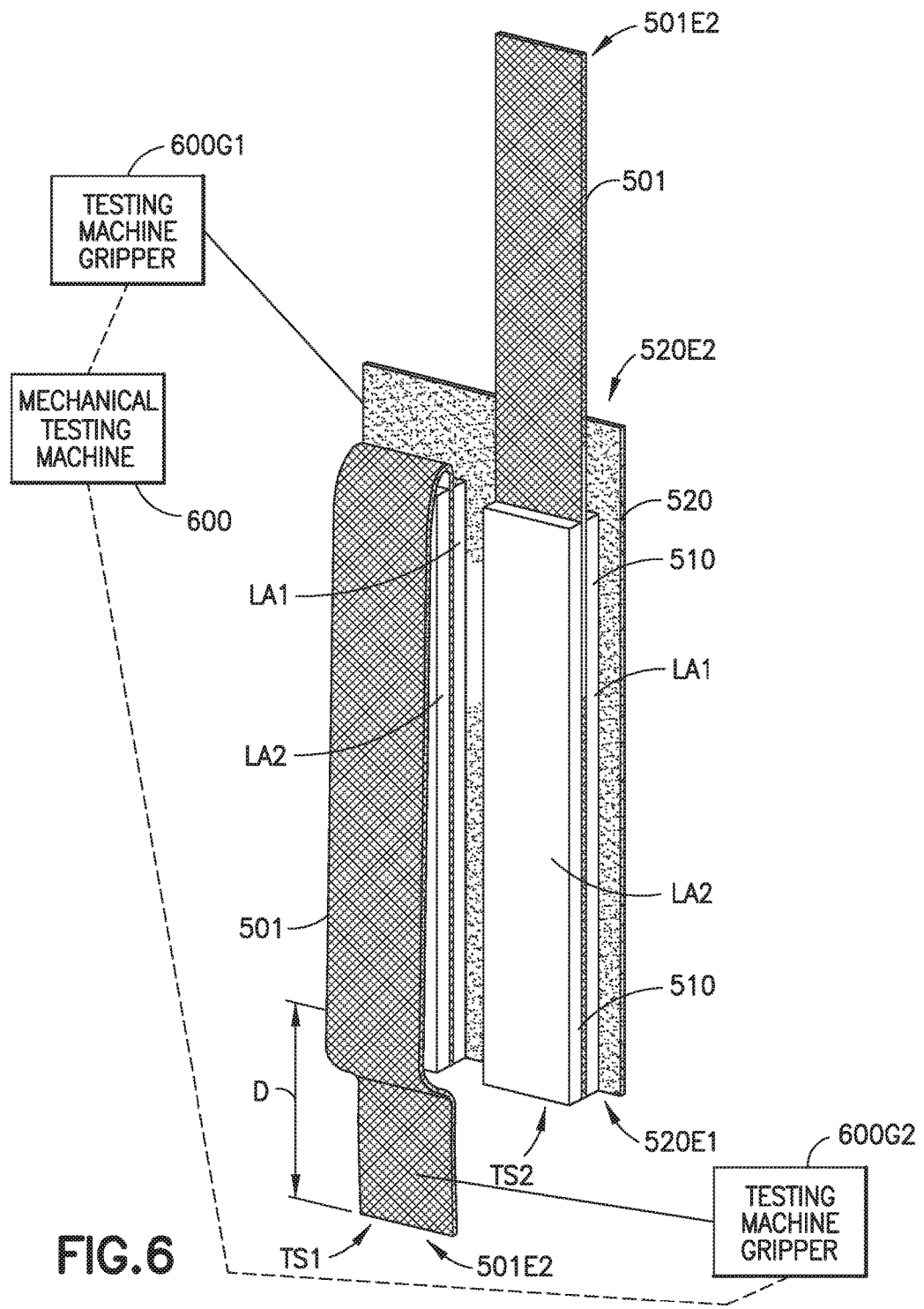
Figure 7A:
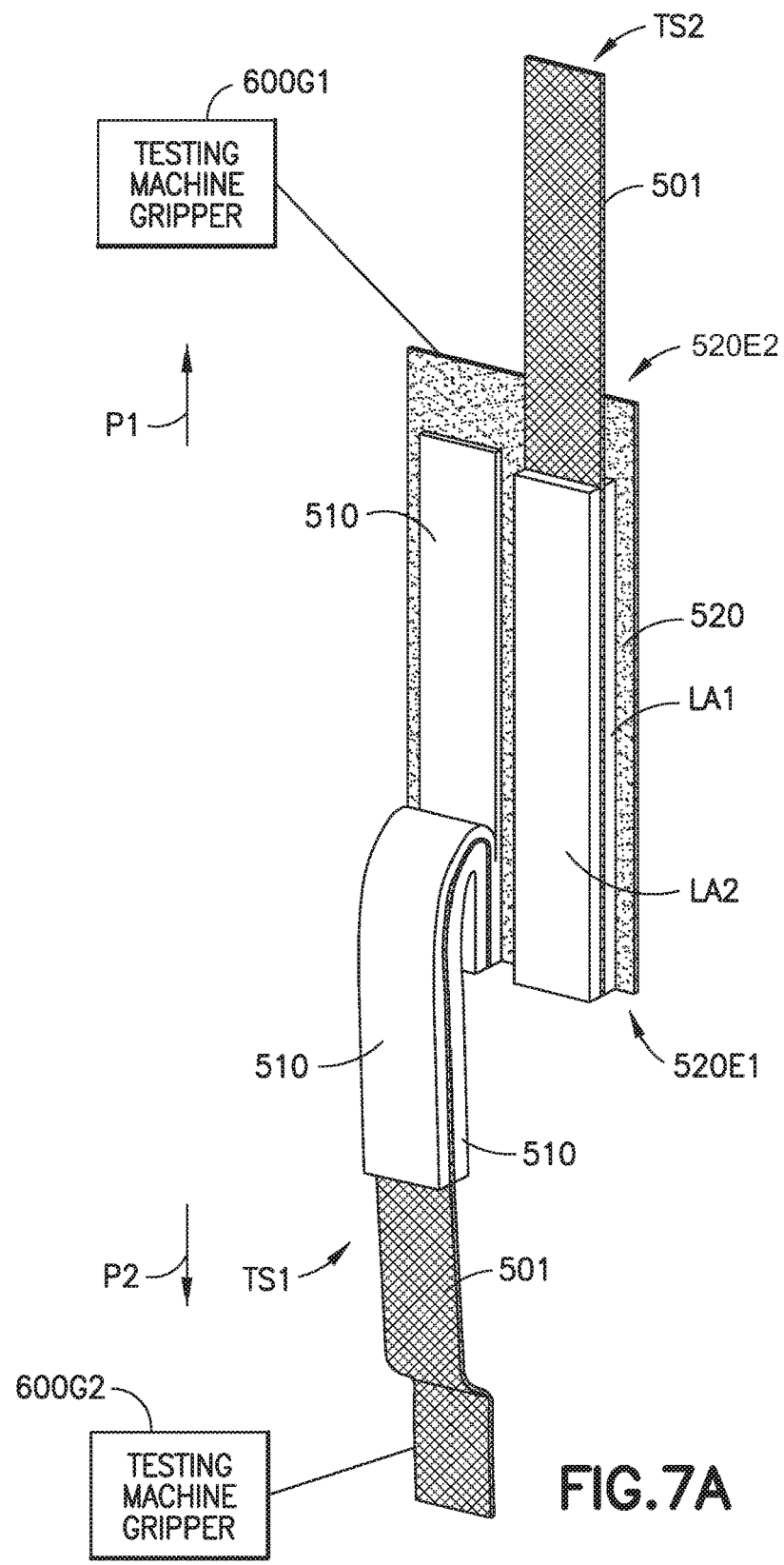
Figure 7B:
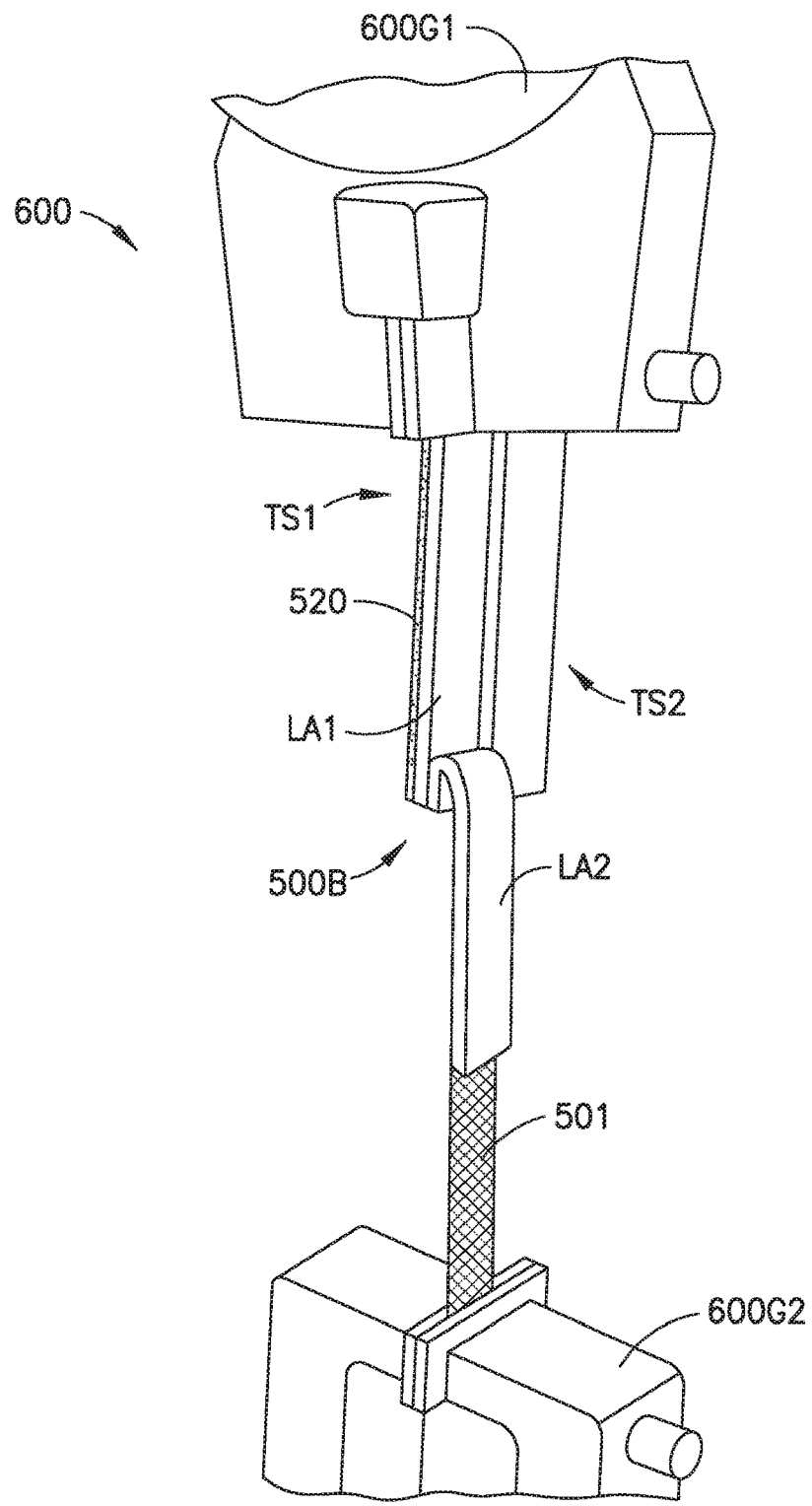
Figure 8:
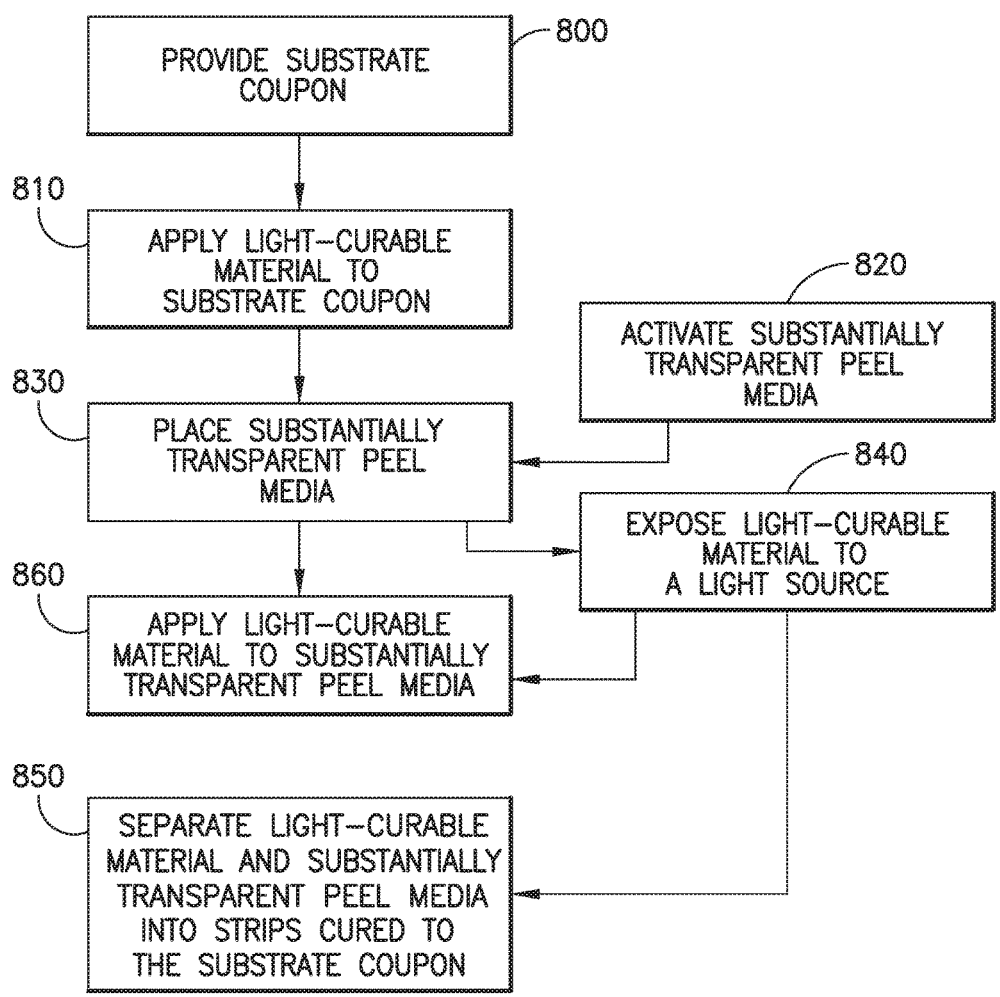
Figure 9:
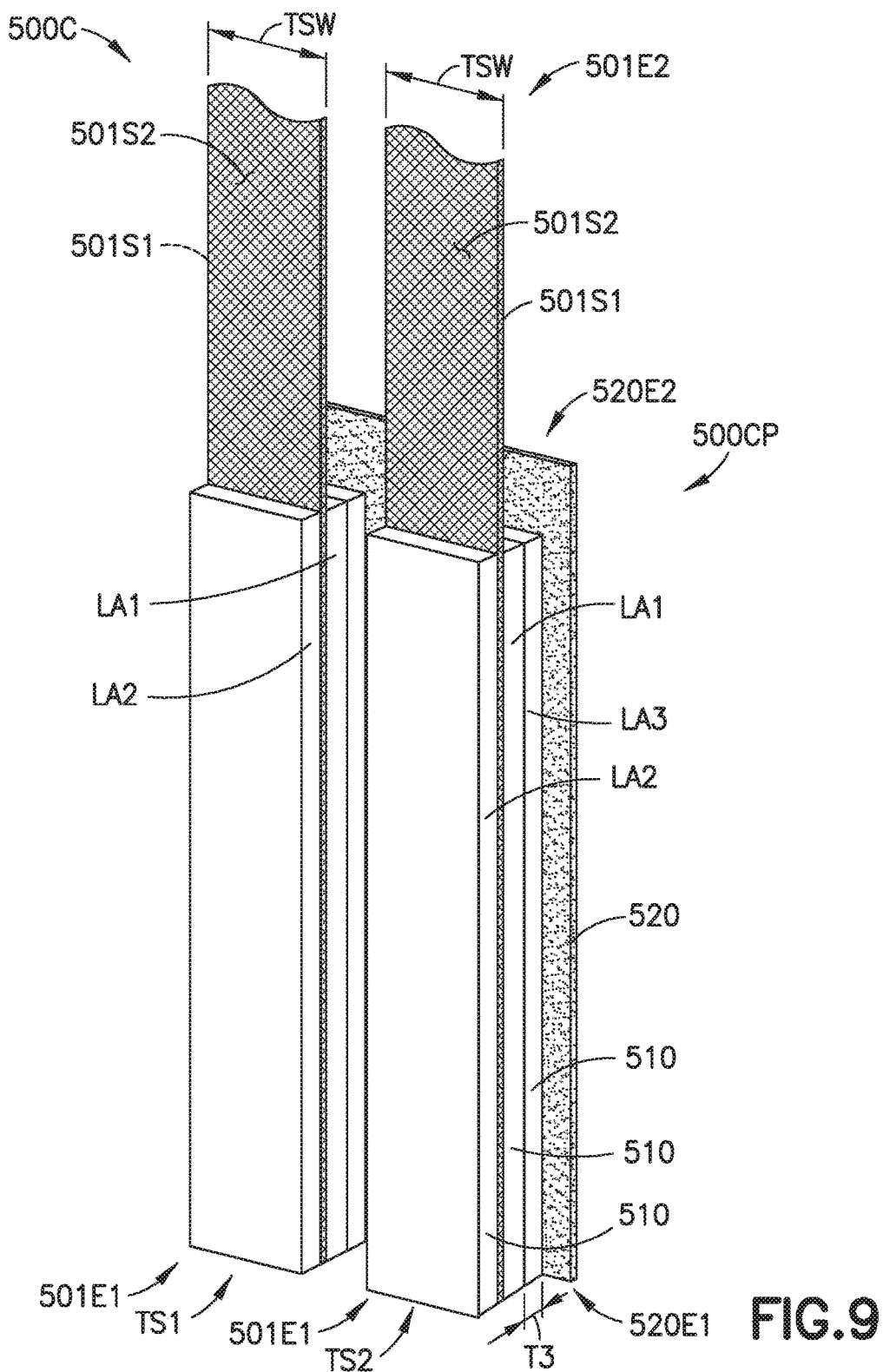

Having thus described examples of the present disclosure in general terms, reference will now be made to the accompanying drawings, which are not necessarily drawn to scale, and wherein like reference characters designate the same or similar parts throughout the several views, and wherein:

FIG. 1 is a perspective view of a portion of a specimen for peel-adhesion testing in accordance with aspects of the present disclosure;

FIG. 2 is a perspective view of a portion of a specimen for peel-adhesion testing in accordance with aspects of the present disclosure;

FIG. 3 is a perspective view of a portion of a specimen for peel-adhesion testing in accordance with aspects of the present disclosure;

FIG. 4 is a perspective view of a portion of a specimen for peel-adhesion testing in accordance with aspects of the present disclosure;

FIG. 5A is a perspective view of a specimen for peel-adhesion testing in accordance with aspects of the present disclosure;

FIG. 5B is a perspective view of a specimen for peel-adhesion testing in accordance with aspects of the present disclosure;

FIG. 6 is a perspective view of the specimen for peel-adhesion testing of FIG. 5 in a to be tested configuration in accordance with aspects of the present disclosure;

FIG. 7A is a perspective view of the specimen for peel-adhesion testing of FIG. 5 during testing in accordance with aspects of the present disclosure;

FIG. 7B is a perspective view of the specimen for peel-adhesion testing of FIG. 5 during testing in accordance with aspects of the present disclosure;

FIG. 8 is a flow diagram of a method in accordance with aspects of the present disclosure; and FIG. 9 is a perspective view of a specimen for peel-adhesion testing in accordance with aspects of the present disclosure.

DETAILED DESCRIPTION

Referring to FIGS. 5A and 5B the aspects of the present disclosure provide for specimens 500A, 500B for peel-adhesion testing of light-curable materials 510, such as light-curable adhesives and sealants. The specimens 500A, 500B include a substantially transparent peel media 501 that allow light to pass through the substantially transparent peel media 501 so that the light-curable material 510 of the assembled specimen 500A, 500B can be cured. The specimens 500A, 500B described herein provide for testing the light-curable materials 510 using conventional test equipment and procedures.

Referring to FIGS. 1-5B and 8 the specimens 500A, 500B include a substrate coupon 520, at least one layer (e.g. first layer LA1 and second layer LA2) of light-curable material 510 and a substantially transparent peel media 501. The substrate coupon provided (FIG. 8, Block 800) has a longitudinal length L1 and a lateral width W1 that are suitable for testing the specimen 500A, 500B in a mechanical testing machine 600 (see FIGS. 6 and 7A), such as a tensometer. For exemplary purposes the longitudinal length L1 may be about 6 inches and the lateral width W1 may be about 3 inches; but in other aspects the longitudinal length L1 may be more or less than about 6 inches and the lateral width W1 may be more or less than about 3 inches. The substrate coupon 520 is made of any suitable material for which the adhesion test is to be performed, such as aluminum, titanium, composites, etc. (including any surface treatments of the material). For example, if the light-curable material 510 is to be adhered to aluminum then the substrate coupon 520 would be made of aluminum, noting that any surface treatments to the aluminum would also be present on the substrate coupon 520.

The light-curable material 510 may be any suitable light curable material, such as a light-curable adhesive or light-curable sealant. A first predetermined amount A1 of the light-curable material 510 is applied to the substrate coupon 520 (FIG. 8, Block 810). In one aspect, the first predetermined amount A1 of the light-curable material 510 is applied directly to the substrate coupon 520; while in other aspects an adhesion promoter AP or a "brushcoat" BC is applied to the substrate coupon 520 and the first predetermined amount A1 of the light-curable material 510 is applied to the adhesion promoter or "brushcoat". For example, the substrate coupon 520 may have a layer of adhesion promoter AP applied (by brushing, spraying or other application method) to the substrate coupon 520 before the sealant is applied. The adhesion promoter AP is a material that is typically a brushed-on liquid that is allowed to dry before the sealant is applied. This adhesion promoter AP forms a layer that is very thin compared to a first layer LA1 of light-curable material 510 formed by the first predetermined amount A1 of the light-curable material 510. For example, the layer formed by the adhesion promoter AP may have a thickness of about less than 0.001 inches. The adhesion promoter AP is used to allow some light-curable material 510 to adhere to the substrate coupon 520 or to prevent surface contaminants from reducing adhesive strength of the light-curable material 510. As noted above, the light-curable material 510 can also be applied over a layer of "brushcoat" BC. The brushcoat BC is similar to an adhesion promoter except that the brushcoat is a thin layer (having a thickness of about 0.010 inches or less) of the light-curable material 510 that typically requires some cure time. The brushcoat BC is typically used to prevent surface contaminants from reducing the adhesive strength of the light-curable material 510 but does not typically allow the light-curable material 510 to adhere to surfaces it would otherwise not adhere to.

The first predetermined amount A1 of light-curable material 510 includes a first layer LA1 of uncured light curable material 510 having any suitable thickness T1 (also referred to herein as the first thickness), where the first layer LA1 extends over substantially the entire lateral width W1 of the substrate coupon 520. The first layer LA1 also extends longitudinally from a first end 520E1 of the substrate coupon 520 to a distance X away from the second end 520E2 of the substrate coupon 520. This distance X provides for an exposed area of the substrate coupon 520 that is gripped by the mechanical testing machine 600 during peel-adhesion testing. In one aspect, the thickness T1 of the first layer LA1 of light-curable material 510 is between about 0.10 inches to about 0.20 inches; but in other aspects the thickness T1 may be less than about 0.10 inches or more than about 0.20 inches.

The substantially transparent peel media 501 is constructed of any suitable polymeric material that has a substantially uniform transparent composition. The substantially transparent peel media 501 has a first end 501E1 and a second end 501E2 separated by a longitudinal length L2. The substantially transparent peel media 501 also has a lateral width W2 and includes a first surface 501S1 and a second surface 501S2 spaced from the first surface by a distance T3. The longitudinal length L2 of the substantially transparent peel media 501 is greater than the longitudinal length L1 of the substrate coupon 520. For example, in one aspect, the longitudinal length L2 may be about 12 inches, but in other aspects the longitudinal length L2 may be more or less than about 12 inches as long as the substantially transparent peel media 501 extends past the first end 520E 1 of the substrate coupon 520 a predetermined distance D (see FIG. 6) when the substantially transparent peel media 501 is folded over itself for peel-adhesion testing. The lateral width W2 of the substantially transparent peel media 501 is substantially the same as (but could be greater than) the lateral width W1 of the substrate coupon 520. The thickness T3 of the substantially transparent peel media 501 is about 0.005 inches to about 0.015 inches; but in other aspects, the thickness T3 may be less than about 0.005 inches or more than about 0.015 inches.

One or more of the first surface 501S1 and the second surface 501S2 of the substantially transparent peel media 501 is treated to activate the one or more of the first surface 501S1 and the second surface 501S2 for promoting adhesion to the light-curable material 510 (FIG. 8, Block 820). In one aspect, the first surface 501S1 of the substantially transparent peel media 501 is activated for promoting adhesion of the light-curable material to the first surface 501S1 of the substantially transparent peel media 501. In another aspect, the second surface 501S2 of the substantially transparent peel media 501 is activated for promoting adhesion of the light-curable material to the second surface 501S2 of the substantially transparent peel media 501. In still another aspect, both the first surface 501S1 and the second surface 501S2 of the substantially transparent peel media 501 is activated for promoting adhesion of the light-curable material to both the first surface 501S and the second surface 501S2 of the substantially transparent peel media 501. The first surface 501S1 and/or the second surface 501S2 of the substantially transparent peel media 501 is activated by, one or more of chemical treating, exposure to plasma (e.g. generated from any suitable gas including oxygen, nitrogen, argon, hydrogen, etc.), exposure to corona discharge treatment, exposure to ultra-violet light, and exposure to ozone. The chemical treatment of the first surface 501S1 and/or the second surface 501S2 includes one or more of exposure to acids, bases, and oxidizers. The first surface 501S1 and the second surface 501S2 are cleaned in any suitable manner, such as with a solvent, prior to activation of the first surface 501S1 and/or the second surface 501S2.

The first surface 501S1 of the substantially transparent peel media 501 is placed in contact with the first layer LA1 of the light-curable material 510 (FIG. 8, Block 830) disposed on the substrate coupon 520 while the light-curable material 510 is still wet (e.g. before curing). The light-curable material 510 disposed between the substrate coupon 520 and the first surface 501 S1 of the substantially transparent peel media 501 is exposed to any suitable light source 300 (FIG. 8, Block 840), such as an ultra-violet light, blue light and/or violet light, to cure the light curable material 510. Here the light curable material 510 is cured to the first surface 501S1 and the substrate coupon 520 with light 300L from the light source 300 passing through the substantially transparent peel media 501. The substantially uniform transparent composition of the substantially transparent peel media 501 provides for curing the light-curable material 510 without any shadowing within the predetermined time period specified for curing the light-curable material 510 (when unobstructed by opaque structures) so that the cure time of the light-curable material 510 for peel-adhesion testing is substantially the same as the cure time of the light-curable material 510 in a manufacturing/production environment (such as when the light-curable material 510 is disposed to fill a joint between adjacent structures and is light-cured within the joint).

Referring to FIGS. 5A and 8, in one aspect, a peel panel 500AP of the of the specimen 500A is formed from the substrate coupon 520 with the substantially transparent peel media 501 and the first layer LA1 of the light-curable material 510 cured to the substrate coupon 520. Here, the light-curable material 510 and the substantially transparent peel media 501 are separated into at least two test strips TS1, TS2 that are cured to the substrate coupon 520 (FIG. 8. Block 850). For example, a portion of the substantially transparent peel media 501 and the light-curable material 510 is removed from the substrate coupon 520 in any suitable manner, such as by machining, cutting, scraping, etc. As can be seen in FIG. 5A a portion of the substantially transparent peel media 501 and the light-curable material 510 is removed to form two test strips TS1, TS2 where each strip has a width of TSW. In one aspect, the width TSW may be about 1 inch, but in other aspects the width TSW may be more or less than about 1 inch. It is important to note that the light-curable material 510 is removed until the substrate coupon 520 is exposed to separate test strip TS1 from test strip TS2 so that peeling of test strip TS1 does not affect the peeling of test strip TS2.

Referring again to FIGS. 3 and 8, as well as FIGS. 4 and 5B, in one aspect, a second predetermined amount A2 of the light-curable material 510 is applied to the second surface 501S2 of the substantially transparent peel media 501 (FIG. 8, Block 860). The second predetermined amount A2 of light-curable material 510 includes a second layer LA2 of uncured light curable material 510 having any suitable thickness T2 (also referred to herein as the second thickness), where the second layer LA2 extends over substantially the entire lateral width W1 of the substrate coupon 520. The second layer LA2 also extends longitudinally from the first end 520E1 of the substrate coupon 520 to the distance X away from the second end 520E2 of the substrate coupon 520. Again, as described above, this distance X provides for an exposed area of the substrate coupon 520 that is gripped by the mechanical testing machine 600 during peel-adhesion testing. In one aspect, the thickness T2 of the second layer LA2 of light-curable material 510 is substantially equal to the thickness T1 of the first layer LA1; but in other aspects the thickness T1 and the thickness T2 are different (e.g. thickness T2 is greater than or smaller than thickness T1). In one aspect, first layer LA1 and second layer LA2 are constructed of the same light curable material 510; by in other aspects, first layer LA1 and second layer LA2 are be constructed of different light curable materials (e.g. the light-curable material of first layer LA1 has different properties than the light curable material of second layer LA2).

The light-curable material disposed on the second surface 501S2 of the substantially transparent peel media 501 is exposed to any suitable light source 300 (FIG. 8, Block 840), such as an ultra-violet light, to cure the light curable material 510 to the second surface 501S2. In one aspect, the light curable material 510 of second layer LA2 and the light curable material 510 of first layer LA1 are cured separately. For example, the light-curable material of first layer LA1 is cured prior to the application of the light-curable material of second layer LA2. In other aspects, the light curable material 510 of both first layer LA1 and second layer LA2 are cured substantially simultaneously. For example, light 300L from light source 300 passes through the light-curable material 510 of second layer LA2, the substantially transparent peel media 501, and the light-curable material 510 of first layer LA1 to the substrate coupon 520 so that the light curable material of both first layer LA1 and second layer LA2 are cured substantially simultaneously.

Where the specimen 500B includes the first layer LA1 and the second layer LA2 of the light-curable material 510 the substantially transparent peel media 501 provides a barrier between the first layer LA1 and the second layer LA2. For example, where the light-curable material 510 is moisture sensitive, the substantially transparent peel media 501 may block moisture diffusion between the first layer LA1 and the second layer LA2. The substantially transparent peel media 501 also provides test results having lower variability (e.g. consistent adhesion between the first and second surfaces 501S1m 501S2 and the light-curable material 510) between peel-adhesion tests than, for example, wire mesh.

In a manner similar to that described above, a peel panel 500BP of the of the specimen 500B is formed from the substrate coupon 520 with the substantially transparent peel media 501, the first layer LA1 of the light-curable material 510, and the second layer LA2 of the light-curable material 510, cured to the substrate coupon 520. Here, the light-curable material 510 and the substantially transparent peel media 501 are separated into the at least two test strips TS1, TS2 that are cured to the substrate coupon 520 (FIG. 8. Block 850). For example, a portion of the substantially transparent peel media 501 and the light-curable material 510 is removed from the substrate coupon 520 in any suitable manner, such as by machining, cutting, scraping, etc. As can be seen in FIG. 5B a portion of the substantially transparent peel media 501 and the light-curable material 510 is removed to form the two test strips TS1, TS2 where each strip has a width of TSW. In one aspect, the width TSW may be about 1 inch, but in other aspects the width TSW may be more or less than about 1 inch. It is important to note that the light-curable material 510 is removed until the substrate coupon 520 is exposed to separate test strip TS1 from test strip TS2 so that peeling of test strip TS1 does not affect the peeling of test strip TS2.

Referring to FIG. 9, the aspects of the present disclosure may also be applied to peel panels 500CP formed by specimens 500C that pertain to the reparability of light-curable materials 510. The specimen 500C and the peel panels 500CP formed therefrom are substantially similar to the specimens 500A, 500B and corresponding peel panels 500AP, 500BP described above; however, in this aspect, a third layer LA3 of light-curable material 510 is disposed between the first layer LA and the substrate coupon 520. This third layer LA3 of light-curable material 510 has a thickness T3 between about 0.10 inches to about 0.20 inches; but in other aspects the thickness T3 may be less than about 0.10 inches or more than about 0.20 inches. In this aspect the third layer LA3 of light-curable material 510 is applied to the substrate coupon 520 and is cured. The first layer LA1 of light-curable material and the peel media 501 (and the second layer LA2 of the light-curable material if desired) are applied to the third layer LA3 of light-curable material 510 in the manner described above with respect to specimens 500A. 500B and the peel panels 500AP, 500BP. The light-curable media 510 of the third layer LA3 may be the same or different light-curable media 510 of the first layer LA1 and/or the second layer LA2. The specimens 500C and the peel panels 500CP formed therefrom are designed to test the adhesion of the light-curable material 510 to itself if the light-curable material 510 needs to be repaired or the ability of one light-curable material 510 to repair another different light-curable material 510 without losing adhesion.

As described above, the specimens 500A and 500B prepared in accordance with the aspects of the present disclosure provide for the testing of light-curable materials 510 with conventional peel-adhesion testing equipment in accordance with, for example, conventional peel-adhesion testing standards including Boeing sealant peel adhesion test standard BSS7257 and SAE International sealant testing specification AS5127/1. For example, referring to FIGS. 6, 7A and 7B an exemplary test of specimen 500B will be described, noting that testing of specimen 500A is performed in a substantially similar manner. The second end 501E2 of the substantially transparent peel media 501 of test strip TS1 is folded over itself so that the second end 501E2 is adjacent the first end 501E1 of the substantially transparent peel media 501. The second end 501E2 may extend beyond the first end 520E1 of the substrate coupon 520 by the distance D to allow for gripping of the substantially transparent peel media 501 by the testing machine gripper 600G2. The specimen 500B is placed in the mechanical testing machine 600 by gripping the substrate coupon 520, at the second end 520E2 in the area defined by the distance X, with the testing machine gripper 600G1. The first end 501E1 of the substantially transparent peel media 501 is gripped by the testing machine gripper 600G2. The mechanical testing machine 600 moves testing machine gripper 600G1 in direction P1 and/or testing machine gripper 600G2 in direction P2 so that the substantially transparent peel media 501 and the substrate coupon 520 are pulled in substantially opposite directions (e.g. where the directions are substantially about 180° from each other). The mechanical testing machine 600 measures the force required to pull the substantially transparent peel media 501 and the substrate coupon 520 in opposite directions P1, P2. The percentage of cohesive (e.g. light-curable material 510 is on both the substrate coupon 520 and the substantially transparent peel media 501) or adhesive (e.g. the light-curable material 510 has pulled away from the substrate coupon cleanly and is only on the substantially transparent peel media 501) failure is observed as the substantially transparent peel media 501 is separated from the substrate coupon 520. It is noted that FIGS. 7A and 7B illustrate a cohesive failure of the light-curable material 510 where the light-curable material 510 of layer LA1 remains on both the substrate coupon 520 and the substantially transparent peel media 501 as the substantially transparent peel media 501 is pulled from the substrate coupon 520. The peel-adhesion testing of test strip TS2 of the specimen 500B placed in the mechanical testing machine 600 in a manner substantially similar to that described above and tested in any suitable conventional manner.

The following are provided in accordance with the aspects of the present disclosure:

A1. A method of preparing specimens for peel-adhesion testing, the method comprising:

applying a first predetermined amount of light-curable material to a substrate coupon;

placing a first surface of a substantially transparent peel media in contact with the light-curable material disposed on the substrate coupon, where the substantially transparent peel media includes a second surface spaced from the first surface; and exposing the first predetermined amount of light-curable material disposed between the substrate coupon and the first surface to a light source to cure the first predetermined amount of light-curable material, with light from the light source passing through the substantially transparent peel media to the substrate coupon.

A2. The method of paragraph A1, wherein the first surface of the substantially transparent peel media is activated for promoting adhesion of the light-curable material to the substantially transparent peel media.

A3. The method of paragraph A2, wherein the first surface of the substantially transparent peel media is activated by exposing the first surface to oxygen plasma.

A4. The method of paragraph A2, wherein the first surface of the substantially transparent peel media is activated by corona discharge treating the first surface.

A5. The method of paragraph A2, wherein the first surface of the substantially transparent peel media is activated by exposing the first surface to ultraviolet light.

A6. The method of paragraph A2, wherein the first surface of the substantially transparent peel media is activated by exposing the first surface to ozone.

A7. The method of paragraph A2, wherein the first surface of the substantially transparent peel media is activated by chemically treating the first surface.

A8. The method of paragraph A2, wherein the first surface of the substantially transparent peel media is cleaned prior to activating the first surface.

A9. The method of paragraph A1, further comprising:

applying a second predetermined amount of the light-curable material to the second surface of the substantially transparent peel media; and exposing the second predetermined amount of light-curable material to a light source to cure the second predetermined amount of light-curable material to the second surface of the substantially transparent peel media.

A10. The method of paragraph A9, wherein the second surface of the substantially transparent peel media is activated for promoting adhesion of the light-curable material to the substantially transparent peel media.

A11. The method of paragraph A10, wherein the second surface of the substantially transparent peel media is activated by exposing the second surface to oxygen plasma.

A12. The method of paragraph A10, wherein the second surface of the substantially transparent peel media is activated by corona discharge treating the second surface.

A13. The method of paragraph A10, wherein the second surface of the substantially transparent peel media is activated by exposing the second surface to ultraviolet light.

A14. The method of paragraph A10, wherein the second surface of the substantially transparent peel media is activated by exposing the second surface to ozone.

A15. The method of paragraph A10, wherein the second surface of the substantially transparent peel media is activated by chemically treating the second surface.

A16. The method of paragraph A10, wherein the second surface of the substantially transparent peel media is cleaned prior to activating the second surface.

A17. The method of paragraph A9, wherein the light-curable material disposed between the substrate coupon and the first surface and the light curable material applied to the second surface of the substantially transparent peel media are cured substantially simultaneously.

A18. The method of paragraph A9, wherein a first thickness of the light-curable material disposed between the substrate coupon and the first surface and a second thickness of the light curable material applied to the second surface of the substantially transparent peel media are substantially equal.

A19. The method of paragraph A9, further comprising forming a peel panel by separating the substantially transparent peel media, the first predetermined amount of light-curable material cured to the first surface and the substrate coupon, and the second predetermined amount of light-curable material cured to the second surface into at least two test strips cured to the substrate coupon.

A20. The method of paragraph A1, further comprising forming a peel panel by separating the substantially transparent peel media and the first predetermined amount of light-curable material cured to the first surface and the substrate coupon into at least two test strips cured to the substrate coupon.

A21. The method of paragraph A1, wherein the substantially transparent peel media comprises a polymeric material.

B1. A method of preparing specimens for peel-adhesion testing, the method comprising:

applying a first predetermined amount of light-curable material to a substrate coupon;

activating a first and second surface of a substantially transparent peel media, where the first surface and the second surface are spaced from one another;

placing the first surface of the substantially transparent peel media in contact with the light-curable material disposed on the substrate coupon;

applying a second predetermined amount of the light-curable material to the second surface of the substantially transparent peel media; and exposing the first predetermined amount of light-curable material and the second predetermined amount of light-curable material to a light source so that the first predetermined amount of light-curable material disposed between the substrate coupon and the first surface and the second predetermined amount of light curable material applied to the second surface of the substantially transparent peel media are cured substantially simultaneously with light from the light source passing through the substantially transparent peel media.

B2. The method of paragraph B1, wherein the first surface and the second surface of the substantially transparent peel media are activated for promoting adhesion of the first predetermined amount of light-curable material and the second predetermined amount of light-curable material to the substantially transparent peel media.

B3. The method of paragraph B2, wherein the first surface and the second surface of the substantially transparent peel media are activated by exposing the first surface and the second surface to oxygen plasma.

B4. The method of paragraph B2, wherein the first surface and the second surface of the substantially transparent peel media are activated by corona discharge treating the first surface and the second surface.

B5. The method of paragraph B2, wherein the first surface and the second surface of the substantially transparent peel media are activated by exposing the first surface and the second surface to ultraviolet light.

B6. The method of paragraph B2, wherein the first surface and the second surface of the substantially transparent peel media are activated by exposing the first surface and the second surface to ozone.

B7. The method of paragraph B2, wherein the first surface and the second surface of the substantially transparent peel media are activated by chemically treating the first surface and the second surface.

B8. The method of paragraph B2, wherein the first surface and the second surface of the substantially transparent peel media are cleaned prior to activating the first surface and the second surface.

B9. The method of paragraph B1, wherein a thickness of the first predetermined amount of light-curable material disposed between the substrate coupon and the first surface and a thickness of the second predetermined amount of light curable material applied to the second surface of the substantially transparent peel media are substantially equal.

B10. The method of paragraph B1, further comprising forming a peel panel by separating the substantially transparent peel media, the first predetermined amount of light-curable material cured to the first surface and the substrate coupon, and the second predetermined amount of light-curable material cured to the second surface into at least two test strips cured to the substrate coupon.

B11. The method of paragraph B1, wherein the substantially transparent peel media comprises a polymeric material.

C1. A specimen for peel-adhesion testing, the specimen comprising:

a substrate coupon;

a first predetermined amount of light-curable material disposed on the substrate coupon;

a substantially transparent peel media having a first surface and a second surface spaced from the first surface, where the substantially transparent peel media is configured so that light passing through the substantially transparent peel media from a light source cures the first predetermined amount of light-curable material to both the substrate coupon and the substantially transparent peel media.

C2. The specimen of paragraph C1, further comprising a second predetermined amount of the light-curable material cured to the second surface of the substantially transparent peel media.

C3. The specimen of paragraph C2, wherein a first thickness of the light-curable material disposed between the substrate coupon and the first surface and a second thickness of the light curable material cured to the second surface of the substantially transparent peel media are substantially equal.

C4. The specimen of paragraph C2, wherein the substantially transparent peel media, the first predetermined amount of light-curable material cured to the first surface and the substrate coupon, and the second predetermined amount of light-curable material cured to the second surface are separated into at least two test strips cured to the substrate coupon.

C5. The specimen of paragraph C1, wherein the substantially transparent peel media and the light-curable material cured to the first surface and the substrate coupon are separated into at least two test strips cured to the substrate coupon.

C6. The specimen of paragraph C1, wherein the substantially transparent peel media comprises a polymeric material.

In the figures, referred to above, solid lines, if any, connecting various elements and/or components may represent mechanical, electrical, fluid, optical, electromagnetic, wireless and other couplings and/or combinations thereof. As used herein, "coupled" means associated directly as well as indirectly. For example, a member A may be directly associated with a member B, or may be indirectly associated therewith, e.g., via another member C. It will be understood that not all relationships among the various disclosed elements are necessarily represented. Accordingly, couplings other than those depicted in the drawings may also exist. Dashed lines, if any, connecting blocks designating the various elements and/or components represent couplings similar in function and purpose to those represented by solid lines; however, couplings represented by the dashed lines may either be selectively provided or may relate to alternative examples of the present disclosure. Likewise, elements and/or components, if any, represented with dashed lines, indicate alternative examples of the present disclosure. One or more elements shown in solid and/or dashed lines may be omitted from a particular example without departing from the scope of the present disclosure. Environmental elements, if any, are represented with dotted lines. Virtual (imaginary) elements may also be shown for clarity. Those skilled in the art will appreciate that some of the features illustrated in the figures, may be combined in various ways without the need to include other features described in the figures, other drawing figures, and/or the accompanying disclosure, even though such combination or combinations are not explicitly illustrated herein. Similarly, additional features not limited to the examples presented, may be combined with some or all of the features shown and described herein.

In FIG. 8, referred to above, the blocks may represent operations and/or portions thereof and lines connecting the various blocks do not imply any particular order or dependency of the operations or portions thereof. Blocks represented by dashed lines indicate alternative operations and/or portions thereof. Dashed lines, if any, connecting the various blocks represent alternative dependencies of the operations or portions thereof. It will be understood that not all dependencies among the various disclosed operations are necessarily represented. FIG. 8 and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

In the foregoing description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of e.g., a "first" or lower-numbered item, and/or, e.g., a "third" or higher-numbered item.

Reference herein to "one example" means that one or more feature, structure, or characteristic described in connection with the example is included in at least one implementation. The phrase "one example" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus (es) and method(s) disclosed herein in any combination, and all of such possibilities are intended to be within the scope of the present disclosure.

Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims, if any, are presented for illustrative purposes only and are not intended to limit the scope of the claimed subject matter to the specific examples provided in the present disclosure.

What is claimed is:

1. A method of preparing specimens for peel-adhesion testing, the method comprising:
    applying a first predetermined amount of light-curable material to a substrate coupon;
    placing a first surface of a substantially transparent peel media in contact with the light-curable material disposed on the substrate coupon, where the substantially transparent peel media includes a second surface spaced from the first surface; and
    exposing the first predetermined amount of light-curable material disposed between the substrate coupon and the first surface to a light source to cure the first predetermined amount of light-curable material to both the substrate coupon and the substantially transparent peel media, with light from the light source passing through the substantially transparent peel media to the substrate coupon.

2. The method of claim 1, wherein the first surface of the substantially transparent peel media is activated for promoting adhesion of the light-curable material to the substantially transparent peel media.

3. The method of claim 2, wherein the first surface of the substantially transparent peel media is activated by chemically treating the first surface.

4. The method of claim 1, further comprising:
    applying a second predetermined amount of the light-curable material to the second surface of the substantially transparent peel media; and
    exposing the second predetermined amount of light-curable material to a light source to cure the second predetermined amount of light-curable material to the second surface of the substantially transparent peel media.

5. The method of claim 4, wherein the second surface of the substantially transparent peel media is activated for promoting adhesion of the light-curable material to the substantially transparent peel media.

6. The method of claim 4, wherein the light-curable material disposed between the substrate coupon and the first surface and the light curable material applied to the second surface of the substantially transparent peel media are cured substantially simultaneously.

7. The method of claim 4, wherein a first thickness of the light-curable material disposed between the substrate coupon and the first surface and a second thickness of the light curable material applied to the second surface of the substantially transparent peel media are substantially equal.

8. The method of claim 4, further comprising forming a peel panel by separating the substantially transparent peel media, the first predetermined amount of light-curable material cured to the first surface and the substrate coupon, and the second predetermined amount of light-curable material cured to the second surface into at least two test strips cured to the substrate coupon.

9. The method of claim 1, further comprising forming a peel panel by separating the substantially transparent peel media and the first predetermined amount of light-curable material cured to the first surface and the substrate coupon into at least two test strips cured to the substrate coupon.

10. The method of claim 1, wherein the substantially transparent peel media comprises a polymeric material.

11. A method of preparing specimens for peel-adhesion testing, the method comprising:
    applying a first predetermined amount of light-curable material to a substrate coupon;
    activating a first and second surface of a substantially transparent peel media, where the first surface and the second surface are spaced from one another;
    placing the first surface of the substantially transparent peel media in contact with the light-curable material disposed on the substrate coupon;
    applying a second predetermined amount of the light-curable material to the second surface of the substantially transparent peel media; and
    exposing the first predetermined amount of light-curable material and the second predetermined amount of light-curable material to a light source so that the first predetermined amount of light-curable material disposed between the substrate coupon and the first surface and the second predetermined amount of light curable material applied to the second surface of the substantially transparent peel media are cured substantially simultaneously with light from the light source passing through the substantially transparent peel media.

12. The method of claim 11, wherein the first surface and the second surface of the substantially transparent peel media are activated for promoting adhesion of the first predetermined amount of light-curable material and the second predetermined amount of light-curable material to the substantially transparent peel media.

13. The method of claim 12, wherein the first surface and the second surface of the substantially transparent peel media are activated by exposing the first surface and the second surface to oxygen plasma.

14. The method of claim 12, wherein the first surface and the second surface of the substantially transparent peel media are activated by corona discharge treating the first surface and the second surface.

15. The method of claim 12, wherein the first surface and the second surface of the substantially transparent peel media are activated by exposing the first surface and the second surface to ultraviolet light.

16. The method of claim 12, wherein the first surface and the second surface of the substantially transparent peel media are activated by exposing the first surface and the second surface to ozone.

17. The method of claim 12, wherein the first surface and the second surface of the substantially transparent peel media are activated by chemically treating the first surface and the second surface.

18. The method of claim 11, wherein a thickness of the first predetermined amount of light-curable material disposed between the substrate coupon and the first surface and a thickness of the second predetermined amount of light curable material applied to the second surface of the substantially transparent peel media are substantially equal.

19. The method of claim 11, further comprising forming a peel panel by separating the substantially transparent peel media, the first predetermined amount of light-curable material cured to the first surface and the substrate coupon, and the second predetermined amount of light- curable material cured to the second surface into at least two test strips cured to the substrate coupon.

20. The method of claim 11, wherein the substantially transparent peel media comprises a polymeric material.

* * * * *